United States Patent
Kalb (12)

(10) Patent No.: US 8,075,803 B2
(45) Date of Patent: Dec. 13, 2011

(54) METHOD FOR PRODUCING IONIC LIQUIDS, IONIC SOLIDS OR MIXTURES THEREOF

(76) Inventor: Roland Kalb, Leoben (AT)

( * ) Notice: Subject to any disclaimer, the term of this patent is extended or adjusted under 35 U.S.C. 154(b) by 379 days.

(21) Appl. No.: 10/569,934

(22) PCT Filed: Aug. 19, 2004

(86) PCT No.: PCT/EP2004/009296
§ 371 (c)(1),
(2), (4) Date: Oct. 10, 2006

(87) PCT Pub. No.: WO2005/021484
PCT Pub. Date: Mar. 10, 2005

(65) Prior Publication Data
US 2008/0251759 A1     Oct. 16, 2008

(30) Foreign Application Priority Data

Aug. 27, 2003  (AT) ................. A 1351/2003

(51) Int. Cl.
| | |
|---|---|
| B01F 1/00 | (2006.01) |
| C11D 7/50 | (2006.01) |
| C11D 7/60 | (2006.01) |
| C11D 7/32 | (2006.01) |
| C11D 7/34 | (2006.01) |
| C11D 7/36 | (2006.01) |

(52) U.S. Cl. ........ 252/364; 510/175; 510/176; 510/177; 510/178

(58) Field of Classification Search ............ 252/364; 510/175, 176, 177, 178
See application file for complete search history.

(56) References Cited

U.S. PATENT DOCUMENTS

| | | | |
|---|---|---|---|
| 4,892,944 A | 1/1990 | Mori et al. | |
| 6,175,019 B1 | 1/2001 | Fischer et al. | |
| 6,379,634 B1 * | 4/2002 | Fields et al. | 423/4 |
| 6,624,127 B1 * | 9/2003 | Brask et al. | 510/175 |
| 7,252,791 B2 * | 8/2007 | Wasserscheid et al. | 252/364 |
| 2004/0026666 A1 * | 2/2004 | Chauvin et al. | 252/364 |
| 2004/0035293 A1 * | 2/2004 | Davis, Jr. | 95/140 |
| 2006/0060818 A1 * | 3/2006 | Tempel et al. | 252/181.3 |
| 2006/0090777 A1 * | 5/2006 | Hecht et al. | 134/42 |
| 2006/0094615 A1 * | 5/2006 | Hecht et al. | 510/179 |
| 2006/0094620 A1 * | 5/2006 | Jordan et al. | 510/286 |
| 2006/0189499 A1 * | 8/2006 | Hecht et al. | 510/320 |
| 2008/0033178 A1 * | 2/2008 | Wasserscheid et al. | 546/250 |
| 2008/0149888 A1 * | 6/2008 | Adler et al. | 252/184 |
| 2008/0166243 A1 * | 7/2008 | Kotschan et al. | 417/92 |

FOREIGN PATENT DOCUMENTS

| | | |
|---|---|---|
| EP | 1 182 196 | 2/2002 |
| JP | 2003 313 172 | 11/2003 |
| WO | WO 02/079212 | 10/2002 |
| WO | WO 02 098844 | 12/2002 |
| WO | WO 03/022812 | 3/2003 |
| WO | WO 03/051894 | 6/2003 |
| WO | WO 2004/063383 A1 * | 7/2004 |

OTHER PUBLICATIONS

International Search Report.
Viscontini, et al., "Synthese einiger Methylimino-diessigsäurederivate", Helv. Chim. Acta 35, pp. 451-455 (1952).
Alcade, et al., "Novel Bis-betaines and Betaines within [1₄]meta-Heterophane Frameworks", Chem. Eur. J., vol. 8, No. 2, pp. 474-484 (2002).
Howitz, et al., "Ueber p-Oxy-chinolone und einige Halogenalkylate des ana-Brom-p-Oxychinolins", Chem. Ber., 38 pages 887-892 (1905).
English translation of the International Preliminary Report on Patentability.
International Search Report, Mar. 18, 2005.
English translation of the International Preliminary Report on Patentability, Jul. 10, 2006.
F. Benetollo et al., "Reaction of ketenylidenetriphenylphosphorane, Ph3PC=C=O, with water: formation of methyltriphenylphosphonium hydrogencarbonate," Journal of Organometallic Chemistry 642, pp. 64-70, 2002.
R. Albert et al., "Zur solvensfreien Darstellung von Tetramethylammoniumsalzen: Synthese un Charakterisierung von [N(CH3)4]2[C2O4], [N(CH3)4] [CO3(CH3)], [N(CH3)4] [NO2], [N(CH3)4][CO2H] und [N(CH3)4][O2C(CH2)2CO2 (CH3)]," Zeitschrift fuer anorganishe und allgemeine Chemie 621, pp. 1735-1740, 1995.
M. Ue et al., "Ionic Liquids with Low Melting Points and Their Application to Double-Layer Capacitor Electrolytes," Electrochemical and Solid-State Letters 5 (6) A119-A121, 2002.
M. Verdecchia et al, "A Safe and Mild Synthesis of Organic Carbonates from Alkyl Halides and Tetrabutylammonium Alkyl Carbonates" J. Org. Chem., 67, pp. 8287-8289, 2002.

* cited by examiner

*Primary Examiner* — Douglas Mc Ginty

(57) ABSTRACT

The invention relates to a method for producing ionic liquids and ionic solids which takes recourse to a novel, especially modular production process. According to the inventive method, those salts from an ionic carbonate, hydrocarbonate or monoalkyl or monoaryl carbonate precursor (cationic synthesis module) are produced that comprise the desired quaternary ammonium, phosphonium, sulfonium or the analogous quaternary heteroaromatic cation. This precursor can be produced and stored efficiently and with a high degree of purity.

28 Claims, No Drawings

METHOD FOR PRODUCING IONIC LIQUIDS, IONIC SOLIDS OR MIXTURES THEREOF

CROSS-REFERENCE TO RELATED APPLICATION

The present application is a 35 U.S.C. §371 national phase conversion of PCT/EP2004/009296 filed Aug. 19, 2004, which claims priority of Austrian application no. A 1351/2003 filed Aug. 27, 2003, which are incorporated herein in their entirety.

The invention relates to a process for preparing ionic liquids, ionic solids or mixtures thereof.

Ionic compounds, viz. compounds which are ionic liquids or ionic solids, have extremely interesting properties such as an unmeasurable vapor pressure, a very wide liquidus range, good electrical conductivity and unusual solvation properties. These advantages predestine them for use in various fields of industrial applications. They can thus be used, for example, as solvents (in organic and inorganic synthesis in general, in transition metal catalysis, biocatalysis, phase-transfer catalysis, multiphase reactions, in photochemistry, in polymer synthesis and nanotechnology), as extractants (in liquid-liquid and liquid-gas extraction in general, the desulfurization of crude oil, the removal of heavy metals from wastewater, liquid membrane extraction), as electrolytes (in batteries, fuel cells, capacitors, solar cells, sensors, in electrochemistry, in electroplating, in electrochemical metal working, in electrochemical synthesis in general, in electroorganic synthesis, in nanotechnology), as lubricants, as heat transfer fluids, as gels, as reagents for organic synthesis, in "green chemistry" (substitute for volatile organic compounds), as antistatics, in special applications in analysis (gas chromatography, mass spectroscopy, capillary zone electrophoresis), as liquid crystals, etc. In this regard, reference may be made, for example, to Rogers, Robin D.; Seddon, Kenneth R. (Eds.); Ionic Liquids—Industrial Applications to Green Chemistry, ACS Symposium Series 818, 2002; ISBN 0841237891 and Wasserscheid, Peter; Welton, Tom (Eds.); Ionic Liquids in Synthesis, Wiley-VCH publishers, 2003; ISBN 3527305157.

The optimization of the properties for the particular application can be effected within wide limits by variation of the structure of anion and cation or variation of their combination, which in the case of ionic liquids has given rise to the term "designer solvents" (cf., for example, Freemantle, M.; Chem. Eng. News, 78, 2000, 37). In this context, many unsystematic individual syntheses for the preparation of ionic compounds have been developed on a laboratory and pilot plant scale. Accordingly, the cost of production of these compounds are extremely high and it is not really feasible to use them on an industrial scale.

The production of ionic liquids has to date been possible virtually exclusively on a laboratory or pilot plant scale, and there is no flexible, generally applicable and efficient synthetic method. In particular, a specific process is employed for virtually every desired anion. Starting compounds used in the syntheses are generally alkyl- or aryl-substituted organic nitrogen, phosphorus or sulfur nucleophiles (amines, phosphines, sulfides, heteroaromatics). The synthetic methods known at present are illustrated for the example of the synthesis of quaternary ammonium compounds (see FIG. 1 below):

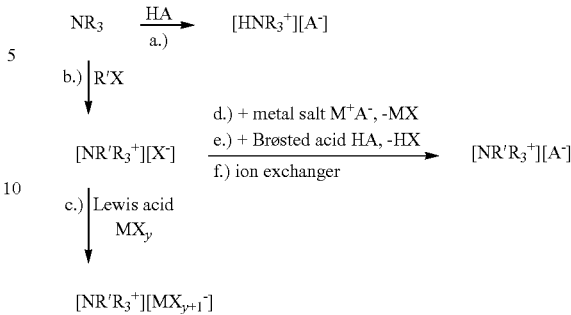

FIG. 1 a. Brønsted Acid/Base Reaction:

An amine $R_3N$ reacts with a protic acid HA to form the salt $[R_3HN^+]$ $[A^-]$. This preparation of ionic liquids is the oldest known (Walden, P., Bull. Acad. Imper. Sci. (St. Petersburg), 1914, 1800) and leads, for example, in the reaction of ethylamine with nitric acid to the formation of ethylammonium nitrate having a melting point of m.p.=13° C. In this case, the cation is not quaternized but merely protonated. These organic salts do not come into question for typical fields of application for ionic liquids because they are thermally and chemically unstable. They are mentioned here merely for the sake of completeness and are not subject matter of the present invention.

b. Alkylation or Arylation to Form a Quaternary Salt:

The amine $R_3N$ is reacted with an alkylating or arylating agent R'X in a nucleophilic substitution to form a quaternary ammonium salt $[NR'R_3^+]$ $[X^-]$ (Wilkes, J. S.; Zaworotko, M. J.; J. Chem. Soc., Chem. Commun., 13, 1992, 965). Typical alkylating agents employed are haloalkanes such as 1-chlorobutane, 1-bromoethane, methyl iodide or dialkyl sulfates such as dimethyl sulfate or diethyl sulfate. Although these alkylating agents are reactive and quickly form the desired product, they are, like all strong alkylating reagents, relatively toxic, some of them are carcinogenic and in the case of the haloalkanes also damage the atmosphere (stratospheric ozone). The ionic compound $[NR'R_3^+]$ $[X^-]$ formed can act as an ionic liquid (m.p.<100° C.) but generally serves as starting material for the following reactions c-f. It is generally strongly hygroscopic.

c. Reaction with a Lewis Acid:

To prepare ionic liquids based on halometalate anions (cf., for example, Wilkes, J. S.; Levisky, J. A.; Wilson, R. A.; Hussey, C. L.; Inorg. Chem. 1982, 21, 1263), the quaternary ammonium salt $[NR'R_3^+]$ $[X^-]$ can be reacted directly with an appropriate Lewis acid (electron pair acceptor) $MX_y$ to give the desired compound $[NR'R_3^+]$ $[MX_{y+1}]$. In the case of the tetrachloroaluminate anion $[AlCl_4]^-$, for example, an appropriate ammonium chloride $[NR'R_3^+]$ $[Cl^-]$ is admixed directly with aluminum chloride $AlCl_3$.

Ionic liquids based on halometalate are extremely water- and oxygen-sensitive, very corrosive and are used only for very specific purposes (for example olefin oligomerization, Friedel-Crafts reactions). Even tiny traces of water lead to hydrolysis and formation of HCl, HBr or HI. Their synthesis is accordingly difficult, not least because of the fact that the starting material $[NR'R_3^+]$ $[X^-]$ is strongly hygroscopic. They are mentioned here merely for the sake of completeness and are not subject matter of the present invention.

d. Anion Exchange Via Metathesis:

The quaternary ammonium salt [NR'R$_3^+$] [X$^-$] formed by alkylation or arylation (see b.) generally does not bear the desired anion. To replace the halide or sulfate anion [X$^-$] by the desired anion [A$^-$], the salt [NR'R$_3^+$] [X$^-$] is admixed in a dry, organic solvent (e.g. acetone, acetonitrile, methylene chloride) with a stoichiometric amount of a metal salt (usually a corresponding alkali metal or alkaline earth metal salt) [M$^+$] [A$^-$] which has the desired anion [A$^-$]. The reaction mixture is typically stirred for a few days to weeks with exclusion of atmospheric moisture. The desired ionic liquid is soluble in the solvent selected and the anion [X$^-$] precipitates as an insoluble, solid metal salt. [M$^+$] [X$^-$] and is removed by filtration. Apart from the very long reaction time and the large amounts of waste [M$^+$] [X$^-$], this process has the disadvantage that dry solvents have to be used in order to achieve complete conversion; otherwise, the salt [M$^+$] [X$^-$] to be removed dissolves in relatively large amounts in the solvent and these traces of halide limit the later use of the ionic liquid (halides are, for example, catalyst poisons; disposal by incineration is problematical).

Carrying out this process in the absence of water is particularly problematical on an industrial scale, since the precursor [NR'R3$^+$] [X$^-$] is generally very hygroscopic and the production process therefore has to be carried out with exclusion of all atmospheric moisture. Although the disadvantages mentioned can be overcome by the use of aqueous solvent systems and silver salts [Ag$^+$] [A$^-$] (resulting in precipitation of silver halides which are very sparingly soluble in water, too), this is ruled out completely on the industrial scale for economic reasons.

A single-stage production process has been filed as a patent a short time ago (Wasserscheid, Peter.; Hilgers, Claus; Boesmann, Andreas; EP 1182197 A1 (Solvent Innovation GmbH, Germany), 2002) which combines the reactions b and d can partly alleviate the problem of exclusion of atmospheric moisture (no isolation of the hygroscopic intermediate [NR'R3$^+$] [X$^-$] is necessary), but the reaction times remain extremely long, waste continues to be obtained and the risk of contamination of the end product by halide ions is always present; in addition, condensation products and impurities formed in the preparation of the intermediate which is not isolated here can only be removed subsequently from the finished product at considerable extra cost.

However, all anion exchange processes via metathesis are, in particular, not generally applicable and work satisfactorily only for very specific combinations of cations and anions. Only if the desired ionic liquid is sufficiently soluble in the solvent (which can often be problematical and large amounts of solvent are sometimes required) and/or the metal salt [M$^+$] [A$^-$] used is significantly more readily soluble in the solvent than the metal salt to be removed, can success be expected. Furthermore, the precipitated salt [M$^+$] [X$^-$] can be partly soluble in the ionic liquid itself.

e. Anion Exchange Via Brønsted Acid:

A further variant of anion exchange is the reaction of the ionic precursor [NR'R3$^+$] [X$^-$] with a Bronsted acid HA. In this case, the associated free acid of the desired anion has to be stronger than the acid HX, so that this reaction, too, is only possible for a few anions [A$^-$]. If HX is a volatile acid, as in the case of the hydrogen halides, this can be removed comparatively easily under reduced pressure (ionic liquids generally have no measurable vapor pressure); if the ionic liquid is hydrophobic, the acid HX can be removed by extraction with water. In all other cases, the isolation of the product is difficult.

f. Anion Exchange on an Ion-Exchange Resin:

Replacement of the ion [X$^-$] by the desired ion [A$^-$] can also be carried out in a generally known process on a conventional anion-exchange resin; however, from an economic point of view, this process is not very feasible on an industrial scale because the maximum loading of a resin is very limited.

It is an object of the invention to provide a process for preparing ionic liquids or ionic solids which allows a very wide range of the substances to be prepared. The ionic liquids or ionic solids should be able to be produced and delivered on time and specific to the customer in industrially relevant quantities and require only a small outlay for storage on the part of the producer.

According to the invention, this object is achieved by the ionic liquids or ionic solids being prepared in a modular fashion from cationic synthesis modules [Q$^+$]$_n$[Y$^{n-}$] and anionic synthesis modules, where

[Q$^+$] is a quaternary ammonium [R$^1$R$^2$R$^3$R$^4$N$^+$], phosphonium [R$^1$R$^2$R$^3$R$^4$P$^+$] or sulfonium [R$^1$R$^2$R$^3$S$^+$] cation or an analogous quaternized nitrogen, phosphorus or sulfur heteroaromatic, where the radicals R$^1$, R$^2$, R$^3$, R$^4$ are all identical, partly identical or different, the radicals R$^1$, R$^2$, R$^3$ and R$^4$ are linear, cyclic, branched, saturated or unsaturated alkyl radicals, monocyclic or polycyclic aromatic or heteroaromatic radicals or derivatives of these radicals which are substituted by further functional groups and R$^1$, R$^2$, R$^3$, R$^4$ may also be joined to one another (polyvalent radical), and [Y$^{n-}$] is a hydrogencarbonate [HCO$_3$], carbonate [CO$_3^{2-}$], monoalkylcarbonate or monoarylcarbonate [ROCO$_2^-$], and where R is a linear, cyclic, branched, saturated or unsaturated alkyl radical, monocyclic or polycyclic aromatic or heteroaromatic or [ROCO$_2^-$] is another monosubstituted carbonate.

The invention comprises an innovative modular production system by means of which an extremely wide range of ionic compounds can be prepared very quickly and simply from ionic synthesis precursors, the cationic synthesis modules, in combination with suitable commercial chemicals, the anionic synthesis modules, so that on-time delivery of industrially relevant quantities is made possible. The invention therefore allows modular production of ionic compounds or mixtures thereof via precursors (cationic synthesis modules) and their reaction with commercial chemicals or other storable intermediates (anionic synthesis modules) in a quick synthesis step which can be carried out immediately before dispatch. The invention makes it possible for a relatively wide product range to be made available systematically by means of few precursors, preferably in combination with chemicals which can be supplied on-time. The production process is also extremely environmentally friendly and is able to provide ionic compounds in accordance with customer wishes and in "tailored" form.

The cationic synthesis modules can be storable precursors which are reacted, in particular at a later point in time, with anionic synthesis modules in a modular production process to form ionic compounds. The outlay for storage is therefore restricted to universally usable precursors, which in view of a huge range of possible combinations, represents an extremely economical and flexible system.

In a preferred embodiment of the invention, the cationic synthesis module [Q$^+$]$_n$[Y$^{n-}$] is treated in a Brønsted acid/base reaction with an n-basic Brønsted acid H$_n$Z as anionic synthesis module, resulting in the carbonate, hydrogencarbonate, monoalkylcarbonate or monoarylcarbonate anion [Y$^{n-}$] being given off as gaseous carbon dioxide and replaced by the desired anion [Z$^{n-}$] and water or, in the case of the monoalkylcarbonates or monoarylcarbonates [ROCO$_2^-$], the corresponding alcohols ROH being formed as by-products. This process is extremely simple, quick, very environmentally friendly and proceeds without any secondary reactions.

In a further variant of the process set forth in claim 8, a suitable metal salt [M$^{2+}$] [Z$^{n-}$]$_{2/n}$ as anionic synthesis module, preferably a strontium, barium, zinc or manganese salt, particularly preferably a calcium salt, is reacted in a type of reaction known as "metathesis" with the carbonate precursor [Q$^+$]$_2$[CO$_3^{2-}$] as cationic synthesis module, resulting in precipitation of sparingly soluble metal carbonate [M$^{2+}$] [CO$_3^{2-}$], preferably strontium, barium, zinc or manganese carbonate, particularly preferably calcium carbonate, and thus in the replacement of the carbonate ion of the carbonate precursor [Q$^+$]$_2$[CO$_3^{2-}$] by the desired anion [Z$^{n-}$]. This alternative can be advantageous when particular industrial chemicals are to be reacted.

According to claim 25, the object mentioned is also achieved in the case of cationic synthesis modules which cannot be synthesized by, for example, the processes of claims 20 to 24 by a preparative process which employs liquid ion exchange.

According to claim 26, the above-mentioned object is also achieved by an alternative process for preparing ionic liquids or ionic solids, in which [Y$^{n-}$] is a hydroxide [OH$^-$] or an alkoxide [RO$^-$], where R is a linear, cyclic, branched, saturated or unsaturated alkyl radical, a monocyclic or polycyclic aromatic or heteroaromatic or a derivative of these radicals which is substituted by further functional groups. This process is advantageous when these hydroxides [Q$^+$] [OH$^-$] or alkoxides [Q$^+$] [RO$^-$] are stable compounds which do not firstly have to be converted into the corresponding stable hydrogencarbonates [Q$^+$] [HCO$_3^-$], carbonates [Q$^+$]$_2$ [CO$_3^{2-}$], monoalkylcarbonates or monoarylcarbonates [Q$^+$] [ROCO$_2^-$] (cf. 2d. reaction of hydroxides and alkoxides with carbon dioxide) but are reacted directly as cationic synthesis modules in a modular production process analogous to the above-described, particularly preferred process with an n-basic Brønsted acid H$_n$Z as anionic synthesis module in a generally known Brønsted acid/base reaction, resulting in the hydroxide or alkoxide being replaced by the desired anion [Z$^-$] and being converted in the case of the hydroxide anion into water (H$_2$O) and in the case of the alkoxide anion into the corresponding alcohol ROH, with the water or alcohol thus formed being separated off from the product [Q$^+$] [Z$^-$] by distillation.

The invention further provides ionic liquids, ionic solids or mixtures thereof which have been prepared by the processes characterized in claims 1 to 28.

Further features, advantages and details of the invention can be derived from the following description. Some of the terms used have the following meanings:

ionic liquids: ionic liquids are, in the sense of the recognized literature (Wasserscheid, Peter; Welton, Tom (Eds.); Ionic Liquids in Synthesis, Wiley-VCH publishers 2003; ISBN 3-527-30515-7), liquid organic salts or salt mixtures which are composed of organic cations and organic or inorganic anions and have melting points of less than 100° C.

ionic solids: the term "ionic solids" encompasses, for the purposes of the present patent application, salts of the type mentioned above under ionic liquids but having melting points of 100° C. and above. Apart from this melting point range set down by definition and the associated state of matter, there is in principle no chemical or physical difference between these and ionic liquids.

ionic compounds: are all ionic liquids and ionic solids within the meaning of the definitions given above.

cationic synthesis modules: are the, preferably storable, ionic precursors [Q$^+$]$_n$[Y$^{n-}$] used for production of the ionic compounds and comprising the desired cation [Q$^+$].

anionic synthesis modules: are the commercial chemicals or other preferably storable intermediates which are reacted with cationic synthesis modules to remove the anion [Y$^{n-}$] of the cationic synthesis modules and replace it by the desired anion [Z$^{n-}$] of the ionic compound [Q$^+$]$_n$[Z$^{n-}$].

synthesis modules: are cationic synthesis modules or anionic synthesis modules.

modular production process: defines the tailored production of ionic compounds and mixtures thereof by means of a combination of appropriate cationic and anionic synthesis modules (building block principle).

The invention provides an extremely versatile and almost universally applicable production process for preparing ionic liquids and ionic solids. In this novel process, the relevant ionic compounds of the general formula [Q$^+$]$_n$[Z$^{n-}$] are produced in a, in contrast to conventional processes, generally applicable, rapid and quantitative synthesis step from a previous ionic precursor [Q$^+$]$_n$[Y$^{n-}$], where [Y$^{n-}$] is a hydrogencarbonate [HCO$_3^-$], carbonate [CO$_3^{2-}$], monoalkylcarbonate or monoarylcarbonate ([ROCO$_2^-$], R=linear, cyclic, branched, saturated or unsaturated alkyl radical, monocyclic or polycyclic aromatic or heteroaromatic) or any other monosubstituted carbonate. The cation [Q$^+$]n concerned is a quaternary ammonium [R$^1$R$^2$R$^3$R$^4$N$^+$], phosphonium [R$^1$R$^2$R$^3$R$^4$P$^+$] or sulfonium [R$^1$R$^2$R$^3$S$^+$] cation or an analogous quaternized nitrogen, phosphorus or sulfur heteroaromatic (cf. FIG. 2), where the radicals R$^1$, R$^2$, R$^3$, R$^4$ can be all identical, partly identical or different. These radicals R$^1$, R$^2$, R$^3$ and R$^4$ can be linear, cyclic, branched, saturated or unsaturated alkyl radicals, monocyclic or polycyclic aromatic or heteroaromatic radicals or derivatives of these radicals which are substituted by further functional groups, with R$^1$, R$^2$, R$^3$, R$^4$ also being able to be joined to one another (polyvalent radical).

FIG. 2 below gives examples of heteroalicyclic and heteroaromatic cations [Q$^+$] (incomplete listing)

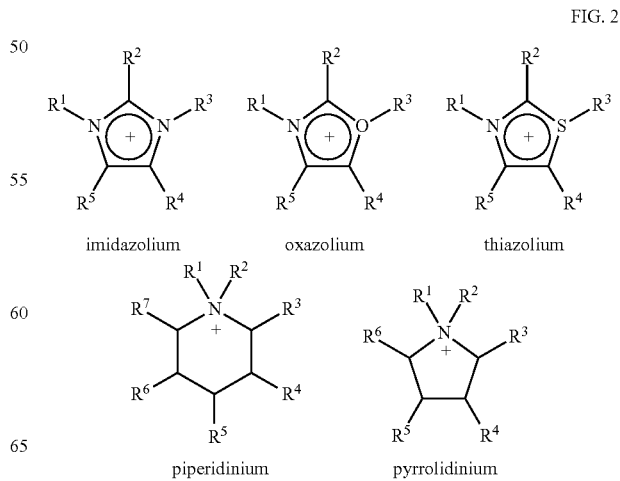

FIG. 2

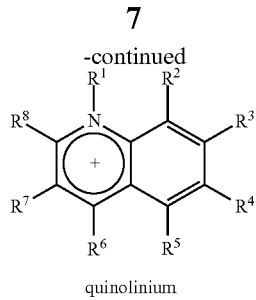

quinolinium

Note: The additional radicals $R^5$, $R^6$, $R^7R^8$ have the same definition as that given for the radicals $R^1$, $R^2$, $R^3$, $R^4$.

The ionic carbonate precursor $[Q^+]_n[Y^{n-}]$ described (cationic synthesis module) is generally stable, can be produced and stored industrially in high purity and is available at any time for the subsequent production processes according to the invention. It can react in two different ways which are described in more detail below under 1a) and 1b) to give the desired product $[Q^+]_n[Z^{n-}]$, with the anion $[Y^{n-}]$ being replaced by the desired anion $[Z^{n-}]$:

1a) Removal of the Carbonate Ion as CO2 in a Bronsted Acid/Base Reaction:

The ionic precursor $[Q^+]_n[Y^{n-}]$ described can be treated in a preferred production process with any stable n-basic Bronsted acid (=proton donor) $H_nZ$ (anionic synthesis module), resulting in a generally known reaction in which the carbonate or hydrogencarbonate anion $[Y^{n-}]$ is given off as gaseous carbon dioxide and water or in the case of monoalkylcarbonates or monoarylcarbonates $[ROCO_2^-]$ the corresponding alcohols ROH are formed as by-products. FIG. 3 shows the corresponding reactions.

FIG. 3

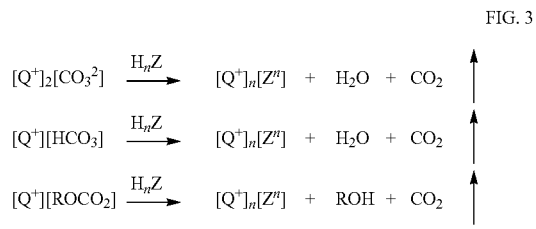

The reaction can be carried out batchwise, semibatchwise or continuously. It generally takes place in aqueous or aqueous-organic solution (with addition of polar auxiliary solvents such as lower alcohols, ketones, sulfoxides, ethers, nitrites, etc.) but can also, if the ionic precursor $[Q^+]_n[Y^{n-}]$ is a liquid, also be carried out in the absence of solvents. The n-basic Bronsted acid $H_nZ$ can be added as such or as a solution in water and/or other solvents in a stoichiometric amount or in excess, with volatile acids $H_nZ$, in particular, preferably being added in excess since they can easily be removed later under reduced pressure (ionic compounds generally have no measurable vapor pressure). In the case of a polybasic acid, the n-basic Bronsted acid $H_nZ$ can also be added in such a stoichiometry that it leads to formation of not the completely dissociated conjugate anion $[Z^{n-}]$ but also the associated protonated anions $[H_mZ^{(n-1)-}]$ (in the case of phosphoric acid $H_3PO_4$, this would be, for example, dihydrogenphosphate $[H_2PO_4^-]$ and hydrogenphosphate $[HPO_4^{2-}]$). The acid/base reaction can be accelerated by application of a vacuum and/or heating, which results in an increase in the reaction rate and continuous removal of carbon dioxide.

The large number of possible Bronsted acids $H_nZ$ which can make many possible ionic compounds $[Q^+]_n[Z^{n-}]$ available in high quality from a single ionic precursor $[Q^+]_n[Y^{n-}]$ in a simple, inexpensive and efficient way in the manner of a "building block system" have given rise to the above-mentioned term "modular production process" which differs significantly from all conventional production processes published to date. The anions $[Z^{n-}]$ and $[H_mZ^{(n-m)-}]$ obtainable thereby are not restricted to the few anions customary up to now, for example tetrafluoroborate $[BF_4^-]$, hexafluorophosphate $[PF_6^-]$, bis(trifluoromethylsulfonyl)imide $[(CF_3SO_2)_2N^-]$, trifluoromethanesulfonate $[CF_3SO_2^-]$, trifluoroacetate $[CF_3CO_3^-]$, methanesulfonate $[CH_3SO_2^-]$, acetate, chloride, bromide, alkylsulfate, etc. (incomplete listing).

1b) Replacement of the Carbonate Ion in a Metathesis Reaction:

A further embodiment of the process of the invention utilizes the sparing solubility of particular metal carbonates (for example calcium, strontium, barium, zinc and magnesium carbonate, incomplete listing):

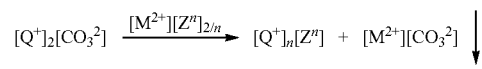

In this case, a suitable metal salt $[M^{2+}][Z^{n-}]_{2/n}$ (preferably a strontium, barium, zinc or manganese salt, particularly preferably a calcium salt) is reacted with the ionic carbonate precursor $[Q^+]_2[CO_3^{2-}]$ in a type of reaction known as "metathesis" (cf. "Anion exchange via metathesis", introductory part of the description). Here too, the driving force of the reaction is the sparing solubility of the precipitating metal carbonate $[M^{2+}][CO_3^{2-}]$; however, these metal carbonates (preferably strontium, barium, zinc or manganese carbonate, particularly preferably calcium carbonate) are sparingly soluble in aqueous solution already, so that the entire metathesis reaction can be carried out in aqueous or aqueous-organic or else organic solution (use of solvents such as alcohols, ketones, esters, sulfoxides, ethers, nitrites, aromatics, etc.) or, if the ionic carbonate precursor $[Q^+]_2[CO_3^{2-}]$ is a liquid, also in the absence of solvents.

In the processes customary hitherto, this has been possible only when using halide precursors and very expensive, often light-sensitive and sometimes toxic silver salts with precipitation of sparingly soluble silver halides or the reaction was carried out using inexpensive metal salts in dry organic solvents with typical reaction times of from days to weeks in the absence of water (cf. "Anion exchange via metathesis", introductory part of the description). In the process of the invention, inexpensive salts such as the particularly preferred calcium salts are utilized instead of expensive silver salts, the reaction proceeds in aqueous medium and is therefore quick and easy to manage, the calcium carbonate, for example, formed is toxicologically unproblematical and troublesome traces of halide are avoided from the beginning.

FIG. 4 below shows the synthesis of 1-butyl-3-methylimidazolium lactate from 1-butyl-3-methylimidazolium carbonate and the industrial chemical calcium lactate as a possible example of this novel process:

FIG. 4

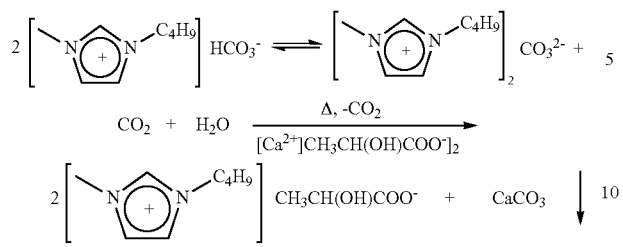

To synthesize the ionic carbonate precursor $[Q^+]_n[Y^{n-}]$ (cationic synthesis module), which can itself be an ionic liquid, it is possible to employ the processes described below under 2a) to 2e), with the radicals described by R, $R^1$, $R^2$, $R^3$, $R^4$, $R^5$, $R'^1$, $R'^2$, $R'^3$, $R'^4$ being able to be all identical, partly identical or different. These radicals R, $R^1$, $R^2$, $R^3$, $R^4$, $R^5$, $R'^1$, $R'^2$, $R'^3$, $R'4$ can be linear, cyclic, branched, saturated or unsaturated alkyl radicals, monocyclic or polycyclic aromatic or heteroaromatic radicals or derivatives of these radicals which are substituted by further functional groups, and R, $R^1$, $R^2$, $R^3$, $R^4$, $R^5$, $R'^1$, $R'^2$, $R'^3$, $R'4$ may also be joined to one another (polyvalent radical).

2a) Quaternization Using Organic Carbonic Esters:

Starting compounds which can be used in this synthesis which is particularly preferred for the preparation of the ionic precursor $[Q^+]_n[Y^{n-}]$ are linear or cyclic amines $NR^1R^2R^3$, phosphines $PR^1R^2R^3$, sulfides $SR^1R^2$ or analogous nitrogen, phosphorus, sulfur heteroaromatics which react with an organic carbonic ester $R^4O(CO)OR^5$ in a nucleophilic substitution reaction (cf. FIG. 5 below):

FIG. 6

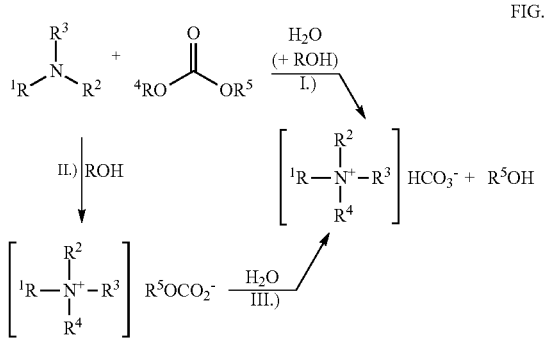

In the case of, for example, an amine NR<1> R<2> R<3>, a corresponding ammonium hydrogencarbonate [R<1> R<2> R<3> R<4> N<+>] [HCO3<–>] is formed directly in aqueous solution (cf. I. in FIG. 5). If necessary, a polar solvent such as low molecular weight alcohols, dimethylformamide, acetonitrile, etc., can be added as solubilizer in addition to water, but a two-phase, purely aqueous reaction mixture procedure with vigorous stirring is likewise possible.

If the reaction is carried out in the polar solvents just mentioned without addition of water (cf. II. in FIG. 5), the corresponding ammonium monoalkylcarbonate or ammonium monoarylcarbonate $[R^1R^2R^3R^4N^+]$ $[R^5OCO_2^-]$ is obtained. This can either be isolated or be converted by hydrolysis (cf. III.) into the corresponding ammonium hydrogencarbonate $[R^1R^2R^3R^4N^+]$ $[HCO_3^-]$. The industrial synthesis of high-purity, quaternary ammonium hydrogencarbonates for the electrochemical production of quaternary ammonium hydroxides is described, for example, in U.S. Pat. No. 4,776,929.

In contrast to the quaternization reagents customary to date, e.g. alkyl or aryl halides, dialkyl or diaryl sulfates, etc. (cf. "Alkylation or arylation to form a quaternary salt" in the introductory part of the description), the organic carbonates $R^4O(CO)OR^5$ used, for example diethyl carbonate, dibutyl carbonate or the cyclic 1,3-dioxolan-2-one (incomplete listing), are unproblematical in terms of human and environmental toxicity (WGK1, Swiss Poisons Class: free, does not damage the atmosphere) and can be disposed of readily.

2b) General Metathesis Using Carbonates and Hydrogen Carbonates:

Some ionic precursors $[Q^+]_n[Y^{n-}]$ which cannot be obtained by quaternization using organic carbonic esters can be prepared by the above-described metathesis reaction (cf. d. "Anion exchange via metathesis", introductory part of the description), as shown in FIG. 6:

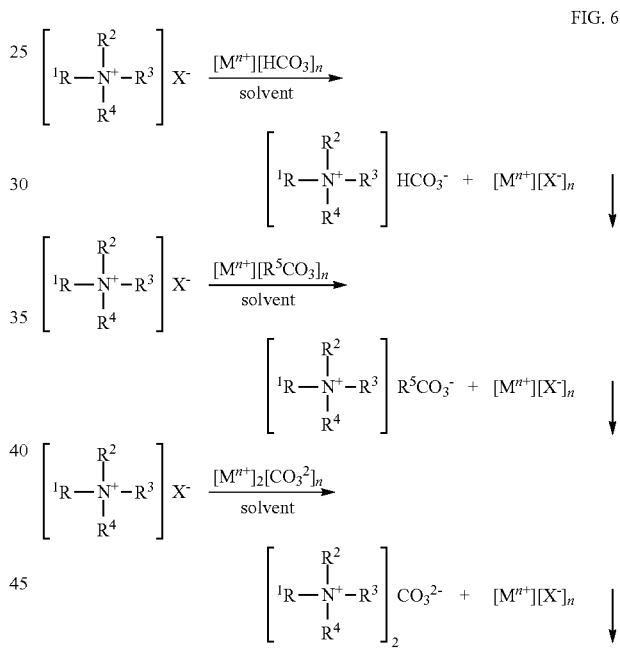

FIG. 6

In the case of, for example, a quaternary ammonium compound $[R^1R^2R^3R^4N^+]$ $[X^-]$ which has been obtained by alkylation or arylation of a tertiary amine $R^1R^2R^3N$ (cf. "Alkylation or arylation to form a quaternary salt" in the introductory part of the description), a hydrogencarbonate $[M^{n+}]$ $[HCO_3^-]$ n, a carbonate $[M^{n+}]_2$ $[CO_3^{2-}]_n$ or a monoalkylcarbonate or monoarylcarbonate $[M^{n+}]$ $[R^5CO_3^-]_n$, where $[M^{n+}]$ is a suitable metal cation, can then be added in a suitable, dry solvent with exclusion of atmospheric moisture. The mixture is stirred and the desired ionic compound is formed in the form of a quaternary ammonium hydrogencarbonate $[R^1R^2R^3R^4N^+]$ $[HCO_3^-]$, a quaternary ammonium carbonate $[R^1R^2R^3R^4N^+]_2[CO_3^{2-}]$ or a quaternary ammonium monoalkylcarbonate or ammonium monoarylcarbonate $[R^1R^2R^3R^4N^+]$ $[R^5CO_3^-]$, with the corresponding alkali metal or alkaline earth metal salt $[M^{n+}]$ $[X^-]$ precipitating as a solid and being removed by filtration. The desired ionic compound is then isolated by distilling off the solvent.

2c) Specific Sulfate Metathesis Using Alkaline Earth Metal Carbonates:

Alkaline earth metal sulfates (with the exception of magnesium sulfate) are sparingly soluble in water (solubilities in g/100 g of water: $CaSO_4$ 0.205 (25° C.); $SrSO_4$ 0.0135 (25° C.); $BaSO_4$ 0.00031 (20° C.); source: CRC Handbook of Chemistry and Physics, 83$^{rd}$ Edition, 2002, ISBN 0-8493-0483-0), while alkaline earth metal hydrogencarbonates display comparatively good solubilities (CD Römpp Chemie Lexikon—Version 1.0, Stuttgart/New York: Georg Thieme Publishers 1995). This ion system is therefore very suitable for preparing quaternary ammonium, phosphonium, sulfonium or analogous heteroaromatic hydrogencarbonates $[Q]^+$ $[HCO_3^-]$ in a specific metathesis reaction. The corresponding alkaline earth metal hydrogencarbonates can easily be produced in aqueous solution from the sparingly soluble alkaline earth metal carbonates by reaction with carbon dioxide, but are unknown as isolated solids. In this case, quaternary ammonium, phosphonium, sulfonium or analogous heteroaromatic sulfates $[Q]_2^+[SO_4^{2-}]$ serve as starting substances for this metathesis and can easily be obtained by alkylation or arylation of linear or cyclic amines $NR^1R^2R^3$, phosphines $PR^1R^2R^3$, sulfides $SR^1R^2$ or analogous nitrogen, phosphorus, sulfur heteroaromatics by means of organic sulfates $R^4O(SO_2)OR^5$ and subsequent hydrolysis:

FIG. 7

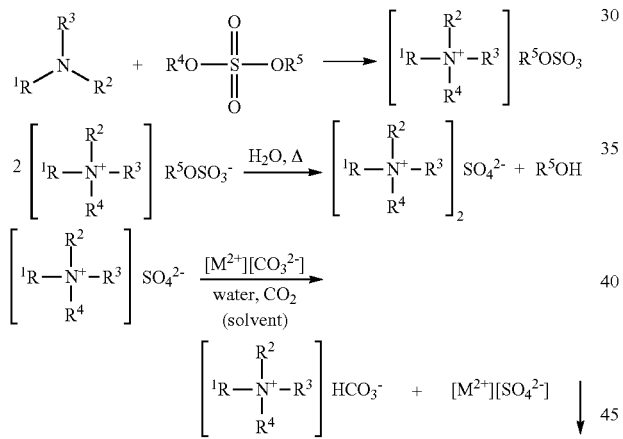

FIG. 7 shows a typical synthesis starting from, by way of example, an amine $NR^1R^2R^3$: the tertiary amine is reacted with an alkyl or aryl sulfate $R^4O(SO_2)OR^5$ in a generally known reaction. This strong alkylating or arylating agent quaternizes the amine to form the corresponding ammonium monoalkylsulfate or ammonium monoarylsulfate $[R^1R^2R^3R^4N^+][R^5SO_4^-]$ which is fully hydrolyzed in a subsequent step in aqueous solution (with addition of polar solvents if necessary) to form the corresponding sulfate $[R^1R^2R^3R^4N^+]_2[SO_4^{2-}]$. The alcohol $R^5OH$ formed in this reaction can remain in the reaction mixture or be removed by distillation. At temperatures of >100° C., low molecular weight sulfates $R^4O(SO_2)OR^4$ such as dimethyl sulfate also react directly to form the corresponding ammonium sulfate $[R^1R^2R^3R^4N^+]_2[SO_4^{2-}]$, so that the hydrolysis step becomes unnecessary.

The ammonium sulfate $[R^1R^2R^3R^4N^+]_2[SO_4^{2-}]$ prepared in this way can remain in the reaction vessel and is then admixed in aqueous solution (or aqueous-organic solution if a polar auxiliary solvent is required to bring it into solution) with an alkaline earth metal carbonate $[M^{2+}][CO_3^{2-}]$, preferably calcium carbonate although strontium and barium carbonate can also be used. While stirring vigorously, gaseous carbon dioxide or solid carbon dioxide ("dry ice") is introduced, resulting in the sparingly soluble alkaline earth metal carbonates being converted into the corresponding readily soluble alkaline earth metal hydrogencarbonates $[M^{2+}][HCO_3^-]_2$.

The dissolved calcium, strontium or barium cations formed in this way react immediately and continually (corresponding to the rate of hydrogencarbonate formation) with the sulfate ions present and form sparingly soluble calcium, strontium or barium sulfate which precipitates as a solid. After the reaction is complete and the precipitated alkaline earth metal sulfate $[M^{2+}][SO_4^{2-}]$ has been removed by filtration, the corresponding ammonium hydrogencarbonate $[R^1R^2R^3R^4N^+][HCO_3^-]$ can be isolated by distilling off the water/solvent mixture, with part or all of this being converted into the corresponding ammonium carbonate $[R^1R^2R^3R^4N^+]_2[CO_3^{2-}]$ by release of carbon dioxide according to the known equilibrium $2[HCO_3^-] \rightarrow [CO_3^{2-}] + CO_2 + H_2O$.

2d) Reaction of Hydroxides and Alkoxides with Carbon Dioxide:

A further possible way of synthesizing the ionic precursor $[Q^+]_n[Y^{n-}]$ is the reaction of quaternary hydroxides $[Q^+][OH^-]$ and alkoxides $[Q^+][RO^-]$ with carbon dioxide (Synthesis, (1), 33-4; 1985 and Journal of Organic Chemistry, 67(23), 8287-8289; 2002). In the case of the hydroxides, water and/or a polar solvent is used as solvent, while in the case of the alkoxides only a polar and aprotic solvent is used when the corresponding monoalkylcarbonates or monoarylcarbonates $[Q^+][ROCO_2^-]$ are to be prepared since the alkoxides otherwise react to form hydroxides and the free alcohols in accordance with $[Q^+][RO^-] + H2O \rightarrow [Q^+][OH^-] + ROH$, which can, however, be reacted again with $CO_2$ to form the hydrogencarbonates $[Q^+][HCO_3^-]$.

In the case of, for example, a quaternary ammonium hydroxide $[R^1R^2R^3R^4N^+][OH^-]$ or ammonium alkoxide $[R^1R^2R^3R^4N^+][R^5O^-]$, the figure shows the synthesis of the quaternary ammonium hydrogencarbonate $[R^1R^2R^3R^4N^+][HCO_3^-]$ or the ammonium monoalkylcarbonate or ammonium monoarylcarbonate $[R^1R^2R^3R^4N^+][R^5OCO_2^-]$.

FIG. 8

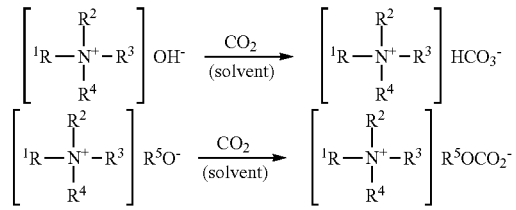

In an alternative to the above processes according to the invention for preparing ionic compounds, the corresponding hydroxides $[Q^+]_2[OH^-]$ or alkoxides $[Q^+][R^5O^-]$ are not firstly converted into the hydrogencarbonates $[Q^+][HCO_3^-]$, carbonates $[Q^+]_2[CO_3^{2-}]$, monoalkylcarbonates or monoarylcarbonates $[Q^+][R^5OCO_2^-]$ ($R^5$ is a linear, cyclic, branched, saturated or unsaturated alkyl radical, a monocyclic or polycyclic aromatic or heteroaromatic or a derivative of these radicals which is substituted by further functional groups) but are instead reacted directly as cationic synthesis modules with an n-basic Brønsted acid $H_nZ$ as anionic synthesis module in a generally known Brønsted acid/base reaction (cf. 1a. Removal of the carbonate ion as $CO_2$ in a Brønsted acid/base reaction) in a modular production process analogous to the above-described, particularly preferred process. Here, the hydroxide or alkoxide anion is replaced by the desired anion [$Z^-$] and converted in the case of the hydroxide anion into water ($H_2O$) and in the case of the alkoxide anion into the corresponding alcohol $R^5OH$, with the water or alcohol $R^5OH$ formed then being separated off from the product [$Q^+$] [$Z^-$] by distillation.

This process is advantageous when these hydroxides [$Q^+$] [$OH^-$] or alkoxides [$Q^+$] [$R^5O^-$] are stable compounds: in contrast to the relatively "mild" hydrogencarbonate, carbonate, monoalkylcarbonate or monoarylcarbonate anion, the hydroxide or alkoxide anion has a significantly higher basicity and nucleophilicity, so that the corresponding cationic synthesis modules [$Q^+$] [$OH^-$] or [$Q^+$][$R^5O^-$] are generally more unstable. However, there are nevertheless sometimes also commercially available hydroxides [$Q^+$] [$OH^-$] or alkoxides [$Q^+$] [$RO^-$] (e.g. aqueous tetraalkyl hydroxide and tetraalkyl alkoxide solutions) which are stable enough for this alternative process and can therefore be reacted directly.

2e) Liquid Ion Exchange Using Medium- to Long-Chain Quaternary Carbonates

Medium- to long-chain quaternary compounds [$Q'^+$]$_n$[$Y''^-$] which have been prepared, for example, in one of the above-described processes 2a-2d, where
[$Q'^+$] is a quaternary ammonium [$R'^1R'^2R'^3R'^4N^+$], phosphonium [$R'^1R'^2R'^3R'^4P^+$] or sulfonium [$R'^1R'^2R'^3S^+$] cation or an analogous quaternized nitrogen, phosphorus or sulfur heteroaromatic,
where the radicals $R'^1$, $R'^2$, $R'^3$, $R'^4$ are all identical, partly identical or different,
the radicals $R'^1$, $R'^2$, $R'^3$ and $R'^4$ are linear, cyclic, branched, saturated or unsaturated alkyl radicals, monocyclic or polycyclic aromatic or heteroaromatic radicals or derivatives of these radicals which are substituted by further functional groups and
$R'^1$, $R'^2$, $R'^3$, $R'^4$ may also be joined to one another (polyvalent radical) and at least one of the radicals $R'^1$, $R'^2$, $R'^3$, $R'^4$ has 4-30 carbon atoms,
and [$Y''^-$] is a hydrogencarbonate [$HCO_3$], carbonate [$CO_3^{2-}$], monoalkylcarbonate or monoarylcarbonate [$R'OCO_2^-$], and
where $R'$ is a linear, cyclic, branched, saturated or unsaturated alkyl radical, monocyclic or polycyclic aromatic or heteroaromatic or [$R'OCO_2^-$] is another monosubstituted carbonate,
are able to undergo liquid ion exchange in aqueous or aqueous-organic solution (addition of polar auxiliary solvents such as lower alcohols, ketones, sulfoxides, ethers, nitrites, etc.): these medium- to long-chain quaternary compounds are still always readily to moderately water-soluble because of the strongly polar, hydrophilic carbonate anions [$Y''^-$] while corresponding compounds [$Q'^+$]$_n$[$X''^-$] having an appropriate chain length are generally nonpolar, hydrophobic and therefore water-immiscible compounds, where
[$X''^-$] can be, for example, a chloride, bromide, iodide, sulfate, phosphate, p-toluenesulfonate, methanesulfonate, trifluoromethanesulfonate, trifluoroacetate anion (incomplete listing) or any other anion which, as described above, forms water-immiscible compounds with cations [$Q^+$].

This behavior can be exploited in order to synthesize ionic precursors [$Q^+$]$_n$[$Y''^-$] (see further above in the description) which cannot be obtained synthetically by, for example, the methods 2a-2d:

here, an appropriate medium- to long-chain quaternary compound [$Q'^+$]$_n$[$Y''^-$] is reacted in aqueous or aqueous-organic solution with a quaternary compound [$Q^+$]$_n$[$X''^-$] which has been prepared by classical, generally known quaternization of a corresponding linear or cyclic amine $NR^1R^2R^3$, phosphine $PR^1R^2R^3$, sulfide $SR^1R^2$ or analogous nitrogen, phosphorus, sulfur heteroaromatics with, for example, an alkyl or aryl halide, p-toluenesulfonate, methanesulfonate, trifluoromethanesulfonate, trifluoroacetate or dialkyl sulfate or diaryl sulfate (incomplete listing) and bears the desired cation [$Q^+$]:

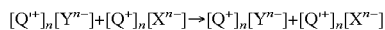

After the reaction, the compound [$Q'^+$]$_n$[$X''^-$] separates out as a liquid, water-immiscible phase (or, depending on the temperature, as a crystalline or wax-like solid) and the desired ionic precursor [$Q^+$]$_n$[$Y''^-$] remains in the aqueous phase from which it can be isolated (after the compound [$Q'^+$]$_n$[$X''^-$] has been separated off) by removal of the water or water/solvent mixture (evaporation, distillation).

A significant advantage of this process is, similarly to the process 2c. "Specific sulfate metathesis using alkaline earth metal carbonates", the use of water or aqueous-organic solvent systems: it is not necessary (as in the case of, for example, the "Anion exchange by metathesis" described under d. in the description of the prior art) to work in the absence of atmospheric moisture and, in addition, fire safety is significantly improved so that industrial production in particular is made considerably easier.

The invention claimed is:

1. A process for preparing ionic liquids, ionic solids or mixtures thereof and having the general formula [$Q^+$]$_n$ [$Z^{n-}$] from cationic synthesis modules including said [$Q^+$] and having the general formula [$Q^+$]$_n$[$Y''^-$] and anionic synthesis modules comprising said [$Z^{n-}$] as their anion, where said [$Q^+$] of said cationic synthesis module is a quaternary ammonium [$R^1R^2R^3R^4N^+$], phosphonium [$R^1R^2R^3R^4P^+$] or sulfonium [$R^1R^2R^3S^+$] cation or an analogous quaternized nitrogen, phosphorus or sulfur heteroaromatic, where the radicals $R^1$, $R^2$, $R^3$, $R^4$ are all identical, partly identical or different, the radicals $R^1$, $R^2$, $R^3$ and $R^4$ are linear, cyclic, branched, saturated or unsaturated alkyl radicals, monocyclic or polycyclic aromatic or heteroaromatic radicals or derivatives of these radicals which are substituted by further functional groups and $R^1$, $R^2$, $R^3$, $R^4$ may also be joined to one another (polyvalent radical), and wherein said [$Y''^-$] of said cationic synthesis module is a hydrogencarbonate [$HCO_3$], carbonate [$CO_3^{2-}$], monoalkylcarbonate or monoarylcarbonate [$ROCO^{2-}$], and where R is a linear, cyclic, branched, saturated or unsaturated alkyl radical, monocyclic or polycyclic aromatic or heteroaromatic or [$ROCO^{2-}$] is another monosubstituted carbonate, and wherein said anionic synthesis module is reacted with said cationic synthesis module [$Q^+$]$_n$[$Y''^-$] to remove the anion [$Y''^-$] of the cationic synthesis module and replace it by said anion [$Z^{n-}$] of said ionic liquids, ionic solids or mixtures.

2. The process as claimed in claim 1, characterized in that preferably a storable cationic synthesis modules are reacted with anionic synthesis modules in a modular production process to give ionic compounds.

3. The process as claimed in claim 1, characterized in that the cationic synthesis module [$Q^+$]$_n$[$Y''^-$] is treated in a Bronsted acid/base reaction with an n-basic Bronsted acid $H_nZ$ as anionic synthesis module, resulting in the carbonate, hydrogencarbonate, monoalkylcarbonate or monoarylcarbonate anion [$Y^{n-}$] being given off as gaseous carbon dioxide and replaced by the desired anion [$Z^{n-}$] and water or, in the case of the monoalkylcarbonates or monoarylcarbonates [$ROCO_2^-$], the corresponding alcohols ROH being formed as by-products.

4. The process as claimed in claim 1, characterized in that n-basic Brønsted acid $H_nZ$ is added as such or as a solution in water and/or other solvents in a stoichiometric amount or in excess, with, in particular, volatile acids $H_nZ$ preferably being added in excess.

5. The process as claimed in claim 1, characterized in that the n-basic Bronsted acid $H_nZ$ can also be added in such a stoichiometry that not the completely dissociated conjugate anion [$Z^{n-}$] but the associated protonated anions [$H_mZ^{n-m-}$], m<n, are formed.

6. The process as claimed in claim 1, characterized in that the reaction is carried out in an aqueous, aqueous/organic or organic solvent (addition of polar solvents such as lower alcohols, ketones, sulfoxides, ethers, nitrites, etc.) or, if the cationic synthesis module [$Q^+$]$_n$[$Y^{n-}$] is liquid at the temperature selected, also in the absence of solvents.

7. The process as claimed in claim 1, characterized in that the acid/base reaction is accelerated by application of a vacuum.

8. The process as claimed in claim 1, characterized in that a suitable metal salt [$M^{2+}$] [$Z^{n-}$]$_{2/n}$ as anionic synthesis module, preferably a strontium, barium, zinc or manganese salt, particularly preferably a calcium salt, is reacted with the carbonate precursor [$Q^+$]$_2$[$CO_3^{2-}$] as cationic synthesis module in a type of reaction known as "metathesis", resulting in sparingly soluble metal carbonate [$M^{2+}$] [$CO_3^{2-}$], preferably strontium, barium, zinc or manganese carbonate, particularly preferably calcium carbonate, being precipitated and the carbonate ion of the carbonate precursor [$Q^+$]$_2$[$CO_3^{2-}$] being replaced by the desired anion [$Z^{n-}$].

9. The process as claimed in claim 1, characterized in that the precipitated sparingly soluble metal carbonate [$M^{2+}$] [$CO_3^{2-}$], preferably strontium, barium, zinc or manganese carbonate, particularly preferably calcium carbonate, is separated from the desired ionic compound [$Q^+$]$_n$ [$Z^{n-}$] by filtration, centrifugation or other suitable methods.

10. The process as claimed in claim 1, characterized in that the reaction is carried out in an aqueous, aqueous/organic or organic solvent (addition of polar solvents such as lower alcohols, ketones, sulfoxides, ethers, nitrites, etc.) or, if the cationic synthesis module [$Q^+$]$_2$[$CO_3^{2-}$] and the desired ionic compound [$Q^+$]$_n$[$Z^{n-}$] are liquid at the temperature selected, also in the absence of solvents.

11. The process as claimed in claim 1, characterized in that the reaction is carried out batchwise, semibatchwise or continuously.

12. The process as claimed in claim 1, characterized in that the reaction mixture is stirred, shaken or mixed in another way.

13. The process as claimed in claim 1, characterized in that the reaction mixture is heated or cooled.

14. The process as claimed in claim 1, characterized in that after the reaction is complete the solvent is removed by distillation, vacuum distillation, thin film evaporation, rotary evaporation or other suitable methods.

15. The process as claimed in claim 1, characterized in that the end product (the ionic compound [$Q^+$]$_n$[$Z^{n-}$]) is freed of impurities by use of adsorbents such as activated carbon, silica gel or aluminum oxide or by application of a vacuum or by extraction.

16. The process as claimed in claim 1, characterized in that commercially available industrial chemicals are used.

17. The process as claimed in claim 1, characterized in that aqueous systems, particularly preferably pure water, are used as solvent.

18. The process as claimed in claim 1, characterized in that the reaction times are from a few minutes to a maximum of one hour.

19. The process as claimed in claim 1, characterized in that the storable cationic synthesis modules are reacted with the anionic synthesis modules only immediately before production of the ionic compound.

20. The process as claimed in claim 1, characterized in that no halogen and/or silver compounds are employed.

21. The process as claimed in claim 1, characterized in that the ionic carbonate precursor [$Q^+$]$_n$[$Y^{n-}$] (cationic synthesis module) is produced by quaternization of linear or cyclic amines $NR^1R^2R^3$, phosphines $PR^1R^2R^3$, sulfides $SR^1R^2$ or analogous nitrogen, phosphorus, sulfur heteroaromatics by means of organic carbonic esters $R^4O(CO)O^5$ in a nucleophilic substitution reaction, where the radicals $R^1$, $R^2$, $R^3$, $R^4$, $R^5$ are all identical, partly identical or different and the radicals are linear, cyclic, branched, saturated or unsaturated alkyl radicals, monocyclic or polycyclic aromatic or heteroaromatic radicals or derivatives of these radicals which are substituted by further functional groups, and $R^1$, $R^2$, $R^3$ and $R^4$, $R^5$ may in each case also be joined to one another (polyvalent radical).

22. The process as claimed in claim 1, characterized in that the ionic carbonate intermediate precursor [$Q^+$]$_n$[$X^{n-}$] (cationic synthesis module) is prepared from an ionic intermediate precursor [$Q^+$]$_n$[$X^{n-}$], where [$X^{n-}$] is a halide, sulfate, sulfonate or any other anion, by "metathesis" and a hydrogencarbonate [$M^{n+}$] [$HCO_3^-$], a carbonate [$M^+$]$_2$[$CO_3^{2-}$]$_n$ or a monoalkylcarbonate or monoarylcarbonate [$M^{n+}$] [$RCO_3^-$]$_n$, where [$M^{n+}$] is a suitable metal cation and R is a linear, cyclic, branched, saturated or unsaturated alkyl radical, a monocyclic or polycyclic aromatic or heteroaromatic radical or a derivative of these radicals which is substituted by further functional groups, is added in a suitable, dry solvent with exclusion of atmospheric moisture and the mixture is stirred to form the desired ionic compound [$Q^+$]$_n$[$Y^{n-}$] (cationic synthesis module), with the corresponding alkali metal or alkaline earth metal salt [$M^{n+}$] [$X^-$] being precipitated as a solid and being removed, in particular, by filtration, centrifugation or other suitable methods.

23. The process as claimed in claim 1, characterized in that [$Y^{n-}$] is a hydrogencarbonate [$HCO_3^-$], [$X^{n-}$] is a sulfate [$SO_4^{2-}$] and [$M^{n+}$] is a strontium or barium or particularly preferably calcium cation and the quaternary ammonium, phosphonium, sulfonium or analogous heteroaromatic sulfate [$Q$]$_2^+$[$SO_4^{2-}$] has been produced by alkylation or arylation of linear or cyclic amines $NR^1R^2R^3$, phosphines $PR^1R^2R^3$, sulfides $SR^1R^2$ or analogous nitrogen, phosphorus, sulfur heteroaromatics by means of organic sulfates $R^4O(CO)O^5$ and the metal salt added to the sulfate [$Q$]$_2^+$[$SO_4^{2-}$] is a hydrogencarbonate [$M^{n+}$][$HCO_3^-$]$_2$ which has been produced beforehand or in situ in aqueous or aqueous-organic solution by reaction of the corresponding sparingly soluble alkaline earth metal carbonate [$M^{n+}$] [$CO_3^{2-}$] with carbon dioxide, with the sparingly soluble strontium, barium or calcium sulfate which precipitates being, in particular, removed by filtration, centrifugation or other suitable methods, where the radicals $R^1$, $R^2$, $R^3$, $R^4$, $R^5$ are all identical, partly identical or different and these radicals are linear, cyclic, branched, saturated or unsaturated alkyl radicals, monocyclic or polycyclic aromatic or heteroaromatic radicals or derivatives of these radicals which are substituted by further functional groups, with $R^1$, $R^2$, $R^3$ and $R^4$, $R^5$ in each case also being able to be joined to one another (polyvalent radical).

24. The process as claimed in claim 1, characterized in that the ionic carbonate precursor $[Q^+]_n[Y^{n-}]$ (cationic synthesis module) is prepared by reaction of quaternary hydroxides $[Q^+][OH^-]$ and alkoxides $[Q^+][RO^-]$ with carbon dioxide, where R is a linear, cyclic, branched, saturated or unsaturated alkyl radical, a monocyclic or polycyclic aromatic or heteroaromatic radical or a derivative of this radical which is substituted by further functional groups.

25. The process as claimed in claim 1, characterized in that the ionic carbonate precursor $[Q^+]_n[Y^{n-}]$ (cationic synthesis module) is prepared by liquid ion exchange between a medium- to long-chain quaternary compound $[Q'^+]_n[Y'']$ and a quaternary compound $[Q^+][Y^{n-}]$ in aqueous or aqueous-organic solution in accordance with

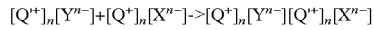

where
- $[Q'^+]$ is a quaternary ammonium $[R'^1R'^2R'^3R'^4N^+]$, phosphonium $[R'^1R'^2R'^3R'^4P^+]$ or sulfonium $[R'^1R'^2R'^3S^+]$ cation or an analogous quaternized nitrogen, phosphorus or sulfur heteroaromatic,
- where the radicals $R'^1$, $R'^2$, $R'^3$, $R'^4$, are all identical, partly identical or different,
- the radicals $R'^1$, $R'^2$, $R'^3$ and $R'^4$, are linear, cyclic, branched, saturated or unsaturated alkyl radicals, monocyclic or polycyclic aromatic or heteroaromatic radicals or derivatives of these radicals which are substituted by further functional groups and
- $R'^1$, $R'^2$, $R'^3$, $R'^4$, may also be joined to one another (polyvalent radical)
- and at least one of the radicals $R'^1$, $R'^2$, $R'^3$, $R'^4$, has 4-30 carbon atoms,
- and $[Y''^-]$ is a hydrogencarbonate $[HCO_3]$, carbonate $[CO_3^-]$, monoalkylcarbonate or monoarylcarbonate $[R'OCO_2^-]$, and
- where R' is a linear, cyclic, branched, saturated or unsaturated alkyl radical, monocyclic or polycyclic aromatic or heteroaromatic or $[R'OCO_2^-]$ is another monosubstituted carbonate,
- where $[Q^+]$ is the desired cation of the ionic precursor, $[X^{n-}]$ can be a chloride, bromide, iodide, sulfate, phosphate, p-toluenesulfonate, methanesulfonate, trifluoromethane-sulfonate, trifluoroacetate anion or any other anion, which is obtained from a classical quaternization reaction of a corresponding linear or cyclic amine $NR^1R^2R^3$, phosphine $PR^1R^2R^3$, sulfide $SR^1R^2$ or analogous nitrogen, phosphorus, sulfur heteroaromatics,
- with $[Q'^+]_n[X^{n-}]$ separating out as water-immiscible phase after liquid ion exchange has occurred
- and the desired ionic precursor $[Q^+]_n[Y^{n-}]$ being present in aqueous or aqueous-organic solution after separation of the water-immiscible phase $[Q^+]_n[Y^{n-}]$
- and this precursor $[Q^+]_n[Y^{n-}]$ finally being able to be isolated by removal of the solvent (evaporation, distillation, etc.).

26. A process for preparing ionic liquids, ionic solids or mixtures thereof and having general formula $[Q^+]_n[Z^{n-}]$ from cationic synthesis modules including said $[Q^+]$ and having the general formula $[Q^+]_n[Y^{n-}]$ and anionic synthesis modules comprising said $[Z^{n-}]$ as their anion,
- where said $[Q^+]$ of said cationic synthesis module is a quaternary ammonium $[R^1R^2R^3R^4N^+]$, phosphonium $[R^1R^2R^3R^4P^+]$ or sulfonium $[R^1R^2R^3S^+]$ cation or an analogous quaternized nitrogen, phosphorus or sulfur heteroaromatic, where the radicals $R^1$, $R^2$, $R^3$, $R^4$ are all identical, partly identical or different,
- the radicals $R^1$, $R^2$, $R^3$, and $R^4$ are linear, cyclic, branched, saturated or unsaturated alkyl radicals, monocyclic or polycyclic aromatic or heteroaromatic radicals or derivatives of these radicals which are substituted by further functional groups and
- $R^1$, $R^2$, $R^3$, $R^4$ may also be joined to one another (polyvalent radical), and said $[Y^{n-}]$ of said cationic synthesis module is an alkoxide $[RO^-]$,
- where R is a linear, cyclic, branched, saturated or unsaturated alkyl radical, a monocyclic or polycyclic aromatic or heteroaromatic or a derivative of these radicals which is substituted by further functional groups, and
- wherein said anionic synthesis module is reacted with said cationic synthesis module to remove the anion $[Y^{n-}]$ of the cationic synthesis module and replace it by said anion $[Z^{n-}]$ of said ionic liquids, ionic solids or mixtures.

27. The process as claimed in claim 26, characterized in that storable cationic synthesis modules are reacted with anionic synthesis modules in a modular production process to give ionic compounds.

28. The process as claimed in claim 26, characterized in that the storable cationic synthesis modules are reacted with the anionic synthesis modules only immediately before production of the ionic compound.

* * * * *